(12) United States Patent
Hammond et al.

(10) Patent No.: US 8,353,825 B2
(45) Date of Patent: Jan. 15, 2013

(54) ACCESS PORTAL INCLUDING SPONGE

(75) Inventors: Richard Hammond, Northford, CT (US); Sally Carter, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 275 days.

(21) Appl. No.: 12/717,203

(22) Filed: Mar. 4, 2010

(65) Prior Publication Data

US 2010/0256453 A1    Oct. 7, 2010

Related U.S. Application Data

(60) Provisional application No. 61/165,945, filed on Apr. 2, 2009.

(51) Int. Cl.
*A61B 1/32* (2006.01)
(52) U.S. Cl. .................................. 600/210; 600/203
(58) Field of Classification Search ............. 600/114, 600/115, 201–246; 604/506, 539, 514; 606/108, 606/191, 197–199
See application file for complete search history.

(56) References Cited

U.S. PATENT DOCUMENTS

| | | | | |
|---|---|---|---|---|
| 2,229,071 A * | 1/1941 | Godstrey | ................ | 15/256.6 |
| 3,871,358 A * | 3/1975 | Fukuda et al. | ................ | 600/585 |
| 4,354,490 A * | 10/1982 | Rogers | ................ | 604/403 |
| 4,475,548 A * | 10/1984 | Muto | ................ | 128/207.14 |
| 5,104,389 A * | 4/1992 | Deem et al. | ................ | 604/264 |
| 5,207,656 A * | 5/1993 | Kranys | ................ | 604/256 |
| 5,232,451 A | 8/1993 | Freitas et al. | | |
| 5,401,248 A | 3/1995 | Bencini | | |
| 5,460,616 A * | 10/1995 | Weinstein et al. | ........ | 604/167.03 |
| 5,599,292 A | 2/1997 | Yoon | | |
| 5,599,305 A * | 2/1997 | Hermann et al. | .......... | 604/95.04 |
| 5,643,227 A * | 7/1997 | Stevens | ................ | 604/264 |
| 5,743,884 A * | 4/1998 | Hasson et al. | .......... | 604/167.02 |
| 5,882,345 A | 3/1999 | Yoon | | |
| 5,989,233 A | 11/1999 | Yoon | | |
| 7,101,353 B2 * | 9/2006 | Lui et al. | ................ | 604/167.06 |
| 8,069,523 B2 * | 12/2011 | Vaillancourt et al. | ........ | 15/104.94 |
| 2003/0172941 A1 | 9/2003 | Streifinger et al. | | |
| 2005/0096695 A1 * | 5/2005 | Olich | ................ | 606/213 |
| 2005/0165277 A1 | 7/2005 | Carrillo et al. | | |
| 2008/0051735 A1 * | 2/2008 | Measamer et al. | ............ | 604/265 |
| 2010/0063364 A1 * | 3/2010 | Bonadio et al. | ................ | 600/208 |

FOREIGN PATENT DOCUMENTS

| | | |
|---|---|---|
| EP | 0709108 | 5/1996 |
| EP | 2044898 | 4/2009 |
| EP | 2113215 | 11/2009 |
| EP | 2238923 | 10/2010 |

OTHER PUBLICATIONS

European Search Report for EP 10250717 date of completion is Jul. 29, 2010 (3 pages).
European Search Report dated May 25, 2011 for the corresponding application EP 10251737, date of completion May 16, 2011.

* cited by examiner

*Primary Examiner* — Eduardo C Robert
*Assistant Examiner* — Lynnsy Schneider

(57) ABSTRACT

A surgical access portal includes a seal housing and a sleeve mounted to the sleeve housing having an internal longitudinal passage adapted to provide access to underlying tissue. A seal is in mechanical cooperation with an inner wall of the seal housing and has an opening for reception and passage of a surgical instrument in a substantially sealed relation. A sponge is disposed distally of the seal and absorbs fluids that enter the seal housing.

13 Claims, 3 Drawing Sheets

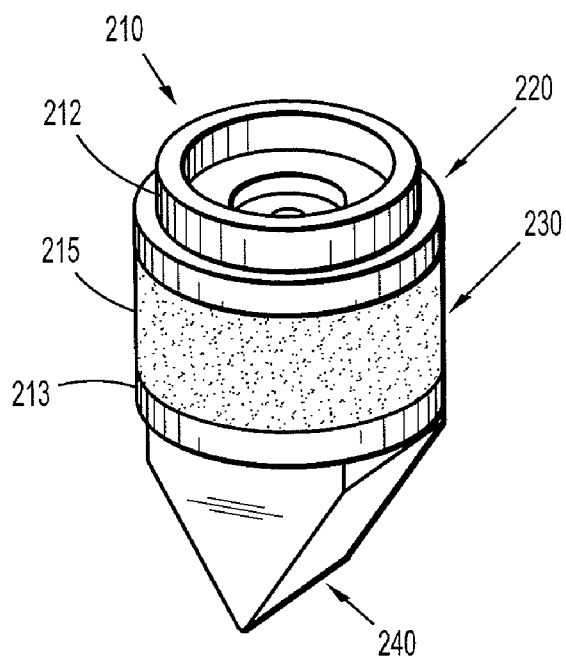
FIG. 4
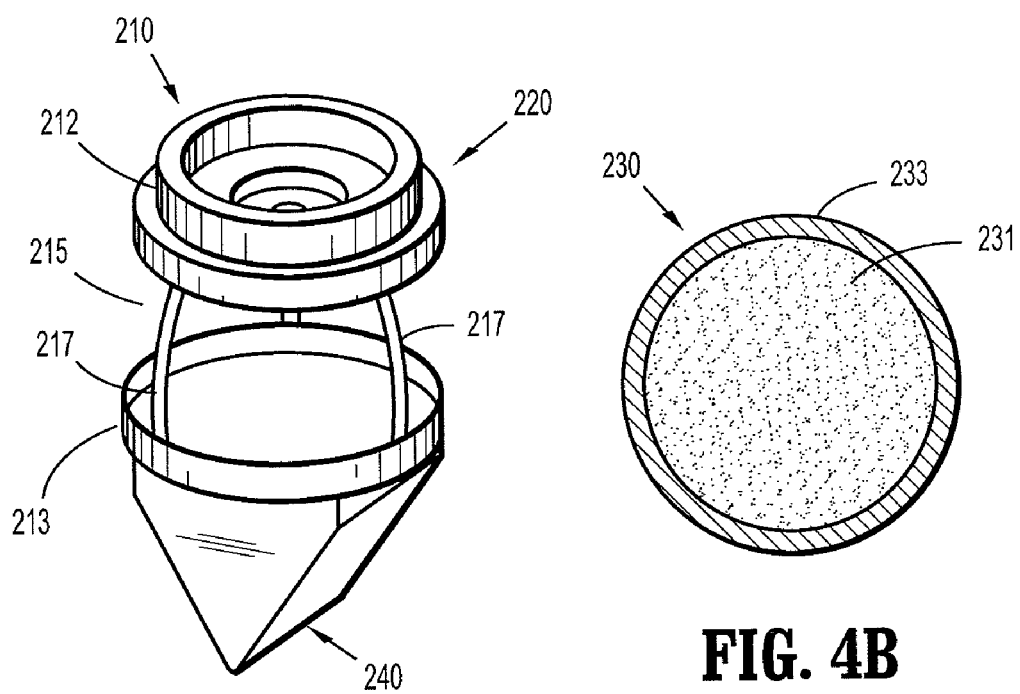
FIG. 4A
FIG. 4B

ACCESS PORTAL INCLUDING SPONGE

CROSS REFERENCE TO RELATED APPLICATION

The present application claims the benefit of and priority to U.S. Provisional Application Ser. No. 61/165,945 filed on Apr. 2, 2009, the entire contents of which are incorporated herein by reference.

BACKGROUND

1. Field of the Disclosure

The present disclosure relates to surgical devices and, more particularly, relates to a surgical access portal apparatus incorporating a sponge for use during a minimally invasive surgical procedure.

2. Description of the Related Art

Minimally invasive surgical procedures including endoscopic, arthroscopic, and laparoscopic procedures permit surgery to be performed on organs, tissues, and vessels far removed from an opening within the tissue. These procedures generally require that any instrumentation inserted into the body be sealed, e.g., provisions may be made to ensure that gases and/or liquids do not enter or exit the body through the incision as, for example, in surgical procedures utilizing insufflating or irrigating fluids. These procedures typically employ surgical instruments which are introduced into the body through a cannula. The cannula has a seal assembly associated therewith. The seal assembly is intended to form a substantially fluid tight seal about the instrument to preserve the integrity of the established surgical site.

SUMMARY

The present disclosure describes a surgical access portal which includes a seal housing and a sleeve mounted to the sleeve housing having an internal longitudinal passage adapted to provide access to underlying tissue. A seal is in mechanical cooperation with an inner wall of the seal housing and has an opening for reception and passage of a surgical instrument in a substantial sealed relation. A sponge is disposed distally of the seal and absorbs fluids that enter the seal housing.

In embodiments, the seal housing includes proximal and distal ends which are joined by a connection member thereby defining an open center portion. The proximal end includes a seal configured to maintain a fluid-tight interface with a surgical instrument. The distal end includes a valve configured to maintain an air-tight seal in the absence of a surgical instrument. The central portion includes a removable sponge for absorbing fluids that enter the seal housing. The outer surface of the sponge may include a non-porous layer or be coated with a non-porous layer in order to provide an air-tight seal within the seal housing.

BRIEF DESCRIPTION OF THE DRAWINGS

Embodiments of the present disclosure will be better appreciated by reference to the drawings wherein:

FIG. 4 is a perspective view of another embodiment of the seal housing in accordance with the principles of the present disclosure;

FIG. 4A is a perspective view of the seal housing of FIG. 4 with the sponge removed therefrom; and FIG. 4B is a top view of the sponge of the seal housing of FIG. 4.

DETAILED DESCRIPTION

The portal apparatus of the present disclosure includes a seal housing either alone or in combination with a cannula assembly. The seal housing of the portal apparatus incorporates a seal with a sponge which, either alone or in combination with a valve, provides a substantial seal between a body cavity of a patient and the outside atmosphere before, during, and after insertion of an object through the portal apparatus. Moreover, the sponge helps prevent fluids from passing into the seal such that functioning of the seal is not degraded.

The seal is capable of accommodating objects of varying diameters, e.g., instruments from about 3 mm to about 15 mm, by providing a fluid tight seal with each instrument when inserted therethrough. The flexibility of the seal greatly facilitates endoscopic surgery, including laparoscopic and arthroscopic procedures, where a variety of instruments having differing diameters are often needed during a single surgical procedure. Examples of surgical instrumentation which may be introduced through the portal apparatus include clip appliers, graspers, dissectors, retractors, staplers, laser probes, photographic devices, endoscopes, laparoscopes, arthroscopes, tubes, and other tools within the purview of those skilled in the art. Such instruments will be collectively referred to herein as "instruments" or "instrumentation."

The seal contemplates the introduction and manipulation of various types of instrumentation adapted for insertion through a trocar, cannula, or portal assembly. A fluid tight interface is maintained via the seal about the instrumentation inserted therethrough to substantially prevent gas and/or liquid leakage from the established surgical site so as to preserve the atmospheric integrity of a surgical procedure. The sponge absorbs fluids introduced into the surgical site, such as a saline irrigant, as well as fluids that have collected on a surgical instrument inserted therethrough. The sponge minimizes or prevents liquid or moisture from reaching the seal and compromising the integrity of the seal.

Figure 1:
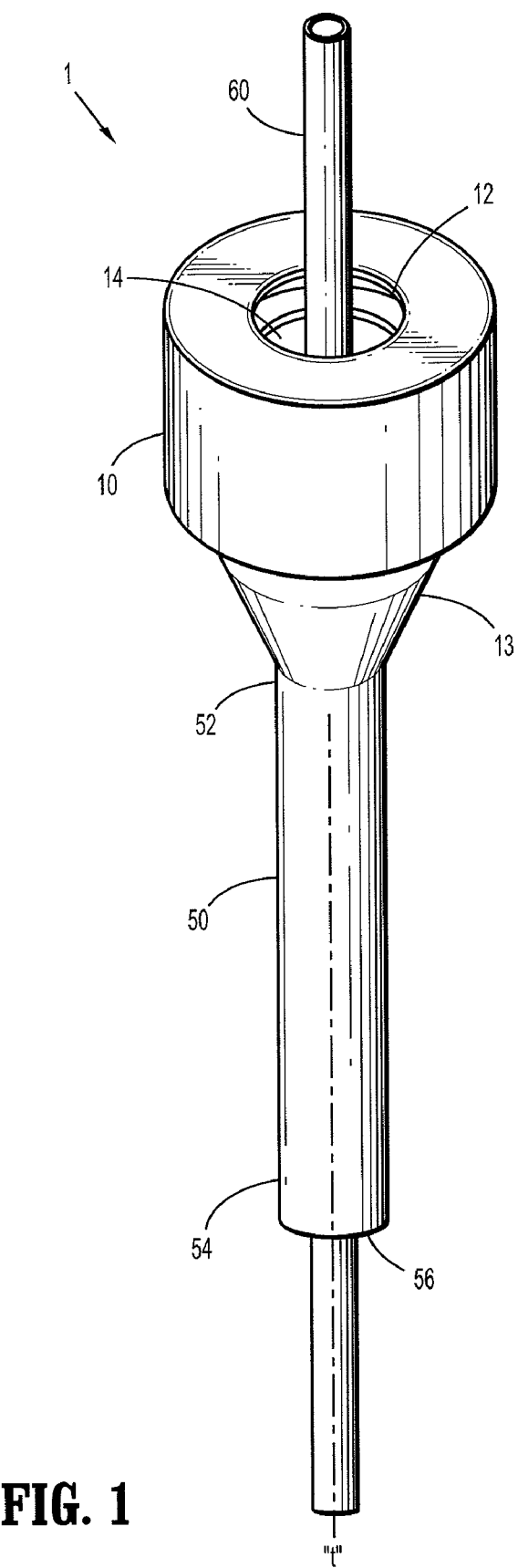
FIG. 1 is a perspective view of a portal apparatus in the form of a seal housing and sleeve including a surgical instrument passed therethrough in accordance with the principles of the present disclosure.

Referring now to the drawings, in which like reference numerals identify identical or substantially similar parts throughout the several views, FIG. 1 illustrates a portal apparatus 1 of the present disclosure incorporating seal housing 10 mounted to sleeve 50. In embodiments, the portal apparatus 1 is particularly adapted for use in arthroscopic surgery where irrigating fluids are pumped into the surgical field. In other embodiments, the portal apparatus 1 is particularly adapted for use in laparoscopic surgery where the peritoneal cavity is insufflated with a suitable gas, e.g., $CO_2$, to raise the cavity wall from the internal organs therein. The sleeve 50 is typically used with an obturator assembly (not shown) which may be a blunt, non-bladed, or sharp pointed instrument positionable within the passageway of the sleeve 50. The obturator assembly is utilized to penetrate the abdominal wall or introduce the sleeve 50 through the abdominal wall, and then subsequently is removed from the sleeve 50 to permit introduction of surgical instrumentation 60 utilized to perform the procedure through the passageway.

Sleeve 50 may be any portal member, such as a cannula or trocar assembly, suitable for the intended purpose of accessing a body cavity and typically defines a passageway permitting introduction of instruments therethrough. Sleeve 50 defines a longitudinal axis "t" extending along the length of sleeve 50 and has proximal (or leading) and distal (or trailing) ends 52, 54, respectively. Sleeve 50 further defines an internal longitudinal passageway 56 dimensioned to permit passage of surgical instrumentation 60. Sleeve 50 may be formed of any suitable medical grade material, such as stainless steel or other rigid materials, including polymeric materials, such as polycarbonate, polystyrene, ABS, as well as other materials contemplated by one skilled in the art.

Sleeve 50 may be transparent, translucent, or opaque. The diameter of sleeve 50 may vary, but, typically ranges from about 3 mm to about 18 mm. Sleeve 50 may or may not include means for facilitating retention of the sleeve 50 within tissue. Such means may include a plurality of locking elements, ribs, or other locking arrangements within the purview of those skilled in the art.

Mounted adjacent proximal end 52 of sleeve 50 is seal housing 10. Sleeve 50 may be releasably secured or connected to seal housing 10 by conventional means including a bayonet coupling, a threaded connection, a snap fit, a friction fit, a tongue and groove arrangement, cam-lock mechanisms, ultrasonic welding or any other means envisioned by one skilled in the art including, e.g., adhesive means. Alternatively, seal housing 10 may be permanently secured to sleeve 50. Sleeve 50 may also incorporate an o-ring seal (not shown) disposed between proximal end 52 of sleeve 50 and seal housing 10 to assist in sealing the interior passages of portal apparatus 1.

Figure 2:
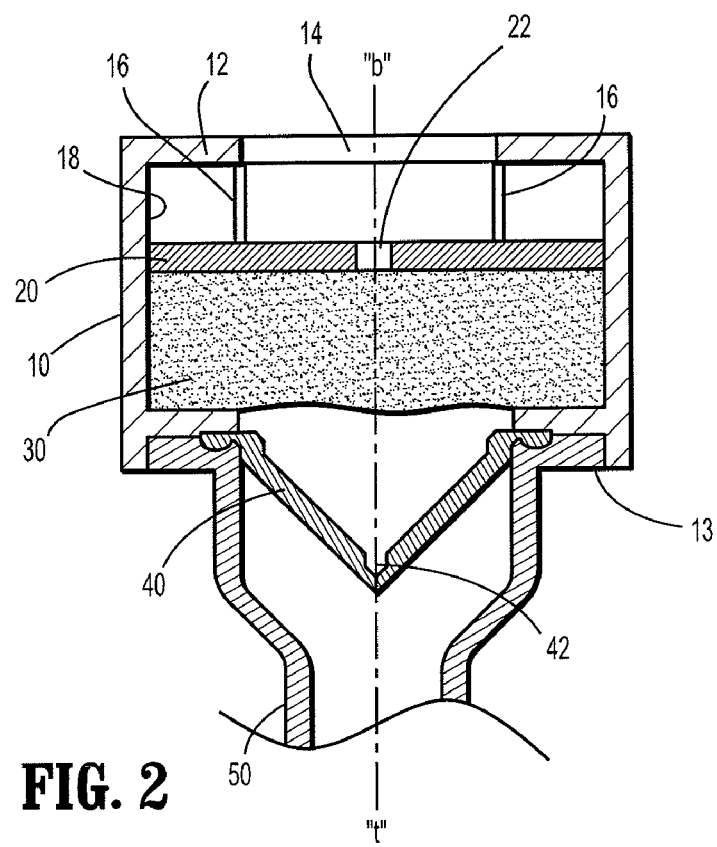
FIG. 2 is a cross-sectional view of the seal housing of the portal apparatus of FIG. 1.

With reference to FIG. 2, in conjunction with FIG. 1, seal housing 10 houses the sealing components, or seal assembly, of the apparatus. Seal housing 10 defines central seal housing axis "b" which, in the illustrated embodiment, is parallel to axis "t" of sleeve 50 and, more specifically, coincident with axis "t" of the sleeve 50 when seal housing 10 is mounted to sleeve 50. Seal housing 10 may be integrally or monolithically formed as a single unit or may incorporate multiple components connected to each other through any of the aforementioned connection means, which, when assembled together, form seal housing 10. Seal housing 10 may be composed of the same or similar materials as sleeve 50 described above.

Seal housing 10 includes proximal end 12 and distal end 13 with inner wall 18 disposed therebetween. Proximal end 12 defines central aperture 14 and optionally, internal annular collar 16 depending from proximal end 12 and coaxially arranged about seal housing axis "b." Central aperture 14 and optional annular collar 16 receive the surgical instrument or object and collectively define an internal dimension or diameter adapted to permit passage of relatively large sized instruments. Annular collar 16 may also limit the degree of lateral or offset movement of the surgical object, e.g., surgical instrument, relative to seal axis "b," by defining an outer limit of movement of the instrument. Distal end 13 defines an opening for passage of a surgical instrument and may incorporate a valve as discussed in further detail below.

Seal housing 10 includes seal 20 disposed proximal to sponge 30. The components may be located about and/or between proximal end 12 and sleeve 50. Seal 20 (e.g., an instrument seal) is generally disc-shaped and may define an aperture, opening, slit, or other passageway 22 for reception and passage of surgical instrument or object 60. Seal 20 is configured to form a substantially fluid-tight fit with surgical instrument 60 passing therethrough. Opening 22 may limit the degree of lateral or offset movement of the surgical object, e.g., surgical instrument. In the illustrated embodiment, seal 20 may be flat or planar. It is envisioned that seal 20 may be any shape for sealing and maintaining the integrity of the established surgical site.

Seal 20 may be formed from a single material or combinations thereof. Seal 20 may be fabricated from a suitable material such as polypropylene, nylon, ABS, polycarbonate, stainless steel, titanium or any other suitable material. As discussed below, seal 20 may also be composed of fabrics, elastomers, foams, gels, combinations thereof, or combinations with other materials to form a layered composite.

Fabric layers may comprise a woven, knitted, braided, or non-woven material of natural or synthetic materials. Fabrics may enhance seal durability and may reduce object or instrument insertion forces. In addition, the fabric may be coated, e.g., on its interior with flexible lubricious materials to facilitate passage of an instrument or other object through the seal.

Optionally, a fabric layer may have a single or multiple intersecting slits. Slits may be substantially linear and extend radially outwardly relative to seal housing axis "b". Other arrangements are envisioned including non-linear slits, serpenditious slits, intersecting slits. Slits may be equidistally and radially spaced about the seal axis. Slits may assist in reducing insertion and withdrawal forces needed to advance the object into the surgical site by reducing radial constriction of the inner areas of fabric layer about the object.

Elastomeric layers are fabricated from a suitable elastomeric or thermoplastic polymer. Elastomeric layers provide protection to the seal by minimizing the potential of puncture with the surgical object, e.g., the instrument, during insertion.

Foam layers may be fabricated from an open or closed cell foam material. Foam segment may assist in sealing about the surgical object. Foam layers may also have sufficient elasticity to bend and deform about the inserted instrument while conforming about the outer dimensioning of the object, e.g., instrument, thereby establishing a fluid tight seal about the object. The foam layers are also sufficiently compliant to absorb off axis motion of the instrument. Moreover, the compliant characteristics of foam layers may substantially minimize the formation of a gap around the instrument during off-set manipulation of the instrument. The presence of a gap would otherwise permit the undesired release of gases from the underlying pneumoperitioneum. The seal arrangements disclosed herein may also be particularly well-suited for applications in which one or more sutures are also extending through the seal alongside the instrument. The presence of such sutures typically causes the surface of the instrument to be irregular and more difficult to seal against, and the foam layers may function to improve the sealing ability of the device by minimizing gaps and conforming to the irregular surface formed by the sutures and the instrument.

In the illustrated embodiment, sponge 30 is disposed distally of, or internal to, seal 20. Sponge 30 includes porous materials that are absorbent. Sponge 30 may include natural, man-made, and/or synthetic materials, or may include synthetic materials manufactured from natural materials, such as synthetic fibers manufactured from natural cellulose. Sponges may be formed from cellulose, cellulose esters such as cellulose acetate and cellulose triacetate, and materials of a cellulosic nature such as cotton or rayon. Sponges may also be formed from polyamides such as nylon, polyolefins such as polyethylene and polypropylene, acrylics, modacrylics, rubber, plastic, thermoplastics, polyvinyl alcohol, polyester, polyurethane, polyether urethane, polyvinyl chloride, vinyl nitrile, silicone, latex, combinations and derivatives thereof, and other absorbent materials within the purview of those skilled in the art. Sponge 30 may also include reticulated, open, and/or closed cell foams.

Seal housing 10 may further include valve 40. In the illustrated embodiment, valve 40 is disposed distally of, or internal to, sponge 30. Valve 40 may be a zero-closure valve such as a duck-bill valve having slit 42 which is adapted to remain closed in the absence of a surgical object and/or in response to insufflation gases of the pressurized cavity. Further, valve 40 helps prevent fluids or debris from entering seal housing 10 when the valve is closed. Fluid pressure on valve 40 may help slit 42 remain closed thereby sealing seal housing 10 from fluids. When an instrument is inserted through valve 40, however, a seal is not always formed around the instrument thereby allowing some fluid to enter seal housing 10 wherein seal 20 helps prevent the fluid from exiting seal housing 10. Sponge 30 therefore is placed adjacent valve 40 and/or between valve 40 and seal 20 to absorb fluid that enters seal housing 10. In the alternative, valve 40 may be a gel seal, balloon valve, or a flapper valve, for example.

Figure 3:
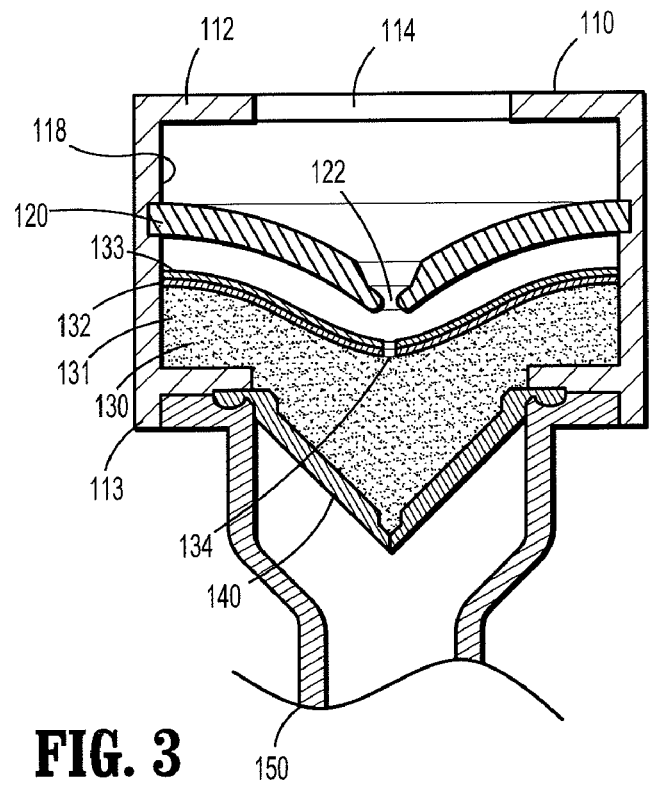
FIG. 3 is a cross-sectional view of another embodiment of the seal assembly of the seal housing.

Referring now to FIG. 3, an alternate embodiment of seal housing 110 is illustrated. Seal 120 and sponge 130 define a generally tapered or funneled profile whereby the inner area of the sponge 130 and seal 120 slope at an oblique angle with respect to seal housing axis "b." The funneled characteristic may assist in guiding the instrument during initial introduction of the instrument or object. Sponge 130 may be any size and shape within the purview of those skilled in the art for absorbing fluids. Sponge 130 may be of a substantially equal diameter to that of inner wall 118 of seal housing 110 or alternatively, have a smaller diameter substantially equal to the diameter of the opening in distal end 113. Sponge 130 may fill the entire space between seal 120 and distal end 113 or any portion thereof. Sponge 130 may be disposed within seal housing 110 in a compressed or biased state. Further, sponge 130 may be layered. Sponge 130 may include any number of layers, each layer being made of any material including fabric, elastomers, foams, gels, and combinations thereof, as discussed above.

In the current embodiment, sponge 130 includes layers 131, 132, and 133. Layer 131 is made of a porous and absorbent material as discussed in FIG. 2. Layer 132 may be a fabric layer to provide support to or reinforcement of sponge 130. Layer 133 may be a closed cell foam layer to provide a non-absorbent backing to sponge 130. The non-porous foam layer 133 may provide an added protective layer for preventing moisture from reaching seal 120. Sponge 130 may include aperture 134 for the passage of a surgical instrument therethrough. Aperture 134 may be a slit or opening of a sufficiently small diameter to grip instruments or objects that are passed therethrough and to absorb moisture or fluid accumulated on the passing instrument. Other combinations of layers are envisioned and within the purview of those skilled in the art.

FIG. 4, in conjunction with FIGS. 4A and 4B, illustrates an alternate embodiment of seal housing 210. Proximal end 212 of seal housing 210 includes seal 220 and distal end 213 of seal housing 210 includes valve 240. Central portion 215 of seal housing 210 includes connection member 217 rather than an inner wall for connecting and spatially separating proximal end 212 and distal end 213. Connection member 217 may be, for example, bars, rods, collars, and the like. Sponge 230 is disposed within central portion 215 in an air-tight manner. Sponge 230 may include an absorbent inner layer 231 for retaining fluid that enters through distal end 213 and a non-porous outer layer 232 for maintaining an air-tight seal within seal housing 210. Alternatively, an outer surface of sponge 230 may be coated with a non-porous substance prior or subsequent to placement within seal housing 210 in order to provide an air-tight seal to seal housing 210. Sponge 230 may be replaced after use or during a surgical procedure. In embodiments, sponge 230 may be replaced during a procedure when a surgical instrument is not present in valve 240. In the absence of the surgical instrument, valve 240 is closed thereby maintaining the integrity of the established surgical site while the sponge 230 is being changed.

The sponge may be manufactured via conventional means. Absorbent sponge layers and fabric, elastomeric, and foam layers may be compression molded. Elastomeric and foam layers may also be subject to heat to at least partially embed the fabric layer into the elastomeric and/or foam layers. Absorbent layers may be stitched with fabric layers. Alternatively, layers may be attached with adhesives, cements, or the like. Once the sponge is assembled or manufactured, an aperture may be punched through the composite with a die punch or made via a molding process. Alternatively, a layered sponge may be provided with cooperative aperture or slits and then assembled via any of the aforementioned methodologies.

The seal, sponge, and/or valve may incorporate a lubricant or a therapeutic or pharmacological agent. Lubricants are within the purview of those skilled in the art for having a smoothness or slipperiness such that it makes a surface relatively free from friction. Examples of therapeutic or pharmacological agents include antimicrobials, antibacterials, hemostatic, moisture-providing agents, such as saline, healing agents, lubricious agents, analgesics, antiseptics, growth factors, and/or anti-inflammatory agents. For example, because the sponge may remain wet with fluid during the course of a procedure, the possibility exists that microorganisms may grow and be transferable back to the patient via contact of different surgical instruments with the sponge. An antibacterial may be applied to the sponge, then, as a means to limit the growth of undesirable microorganisms.

To use portal apparatus 1 in connection with the performance of a surgical task, such as during a laparoscopic procedure, the peritoneal cavity may be insufflated to establish the pneumoperitoneum. Seal housing 10 is mounted to sleeve 50 as discussed above. The assembled portal apparatus 1 is introduced into an insufflated abdominal cavity typically utilizing a sharp or non-blade trocar obturator to access the cavity and the obturator is removed. An instrument may be advanced through portal apparatus 1 by inserting the instrument into aperture 14 of seal housing 10 and through seal 20 whereby the portions defining aperture 22 of the seal 20 stretch to accommodate the instrument in substantial sealed relation therewith. The instrument is distally passed through sponge 30, valve 40, into sleeve 50, and into the body cavity. The desired surgical task is performed with the instrument. During manipulation of the instrument, fluid entering seal housing 10 through valve 40 may be absorbed by sponge 30. Seal 20 maintains a seal about the instrument to prevent formation of any gaps on opposed sides of the instrument.

In arthroscopic procedures, sponge 30 serves to absorb irrigant solution, e.g. saline, utilized during the procedure, e.g. distributed into the joint area, to facilitate removal of the liquid from the seal 20 or valve 40 to thereby maintain adequate function of these components.

It will be understood that various modifications and changes in form and detail may be made to the embodiments of the present disclosure without departing from the spirit and scope of the invention. Therefore, the above description should not be construed as limiting the invention but merely as exemplifications of various embodiments thereof. Those skilled in the art will envision other modifications within the scope and spirit of the present disclosure and the claims appended hereto.

What is claimed is:

1. A seal housing comprising:
    a proximal end including a seal configured to maintain a fluid-tight interface with a surgical instrument;
    a distal end including a valve configured to maintain an air-tight seal in the absence of a surgical instrument;
    a central portion including a plurality of radially spaced connection members connecting the proximal end and the distal end; and
    a removable sponge positioned within the central portion for absorbing fluids that enter the seal housing, the sponge including an absorbent inner layer and a non-porous outer layer.

2. The seal housing according to claim 1, wherein an outer surface of the absorbent inner layer is coated with the non-porous material.

3. The seal housing according to claim 1, wherein the sponge includes layers selected from the group consisting of an absorbent layer, a fabric layer, an elastomeric layer, a foam layer, a gel layer, and combinations thereof.

4. The seal housing according to claim 3, wherein the sponge has an aperture for the passage of a surgical instrument.

5. The seal housing according to claim 1, wherein the sponge is disposed in the seal housing in a compressed state.

6. The seal housing according to claim 1, wherein the sponge includes a therapeutic agent.

7. The access portal according to claim 6, wherein the therapeutic agent is an antibacterial agent.

8. The seal housing of claim 1, wherein the absorbent inner layer of the sponge is configured to receive the surgical instrument therethrough.

9. A seal housing comprising:
    a housing member including:
        a proximal end including a seal configured to maintain a fluid-tight interface with a surgical instrument;
        a distal end; and at least one connection member connecting the proximal and distal ends; and
    a sponge disposed between the proximal end and the distal end in a fluid-tight manner, the sponge including an absorbent inner layer and a non-porous outer layer extending radially outward from the absorbent inner layer, the non-porous outer layer of the sponge forming at least a portion of an outer surface of the housing member wherein the proximal and distal ends remain connected via the at least one connecting member in the absence of the sponge.

10. The seal housing according to claim 9, wherein the distal end includes a valve.

11. The seal housing according to claim 9, wherein the at least one connection member is one of a bar and a rod.

12. The seal housing of claim 9, wherein the sponge is removable from the seal housing.

13. The seal housing of claim 9, wherein the absorbent inner layer of the sponge is configured to receive the surgical instrument therethrough.

* * * * *